(12) United States Patent
Urman et al.

(10) Patent No.: US 10,643,345 B2
(45) Date of Patent: May 5, 2020

(54) METHOD AND SYSTEM FOR DETERMINING LOCATIONS OF ELECTRODES ON A PATIENT BODY

(71) Applicant: BIOSENSE WEBSTER (ISRAEL) LTD., Yokneam (IL)

(72) Inventors: Roy Urman, Karkur (IL); Ronen Krupnik, Karmiel (IL); Liron Shmuel Mizrahi, Kiryat Bialik (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 16/524,486

(22) Filed: Jul. 29, 2019

(65) Prior Publication Data

US 2019/0347818 A1 Nov. 14, 2019

Related U.S. Application Data

(63) Continuation of application No. 15/130,110, filed on Apr. 15, 2016, now Pat. No. 10,410,369.

(51) Int. Cl.
| | |
|---|---|
| *H04N 7/18* | (2006.01) |
| *G06T 7/60* | (2017.01) |
| *A61B 5/00* | (2006.01) |
| *A61B 5/0408* | (2006.01) |
| *A61B 5/06* | (2006.01) |
| *A61B 5/107* | (2006.01) |
| *A61B 5/053* | (2006.01) |
| *G06T 19/00* | (2011.01) |
| *A61B 5/042* | (2006.01) |

(52) U.S. Cl.
CPC .............. *G06T 7/60* (2013.01); *A61B 5/0077* (2013.01); *A61B 5/0408* (2013.01); *A61B 5/0531* (2013.01); *A61B 5/061* (2013.01); *A61B 5/1075* (2013.01); *G06T 19/006* (2013.01); *A61B 5/042* (2013.01); *G06T 2207/30196* (2013.01)

(58) Field of Classification Search
USPC ......................................................... 382/128
See application file for complete search history.

(56) References Cited

U.S. PATENT DOCUMENTS

| | | |
|---|---|---|
| 6,173,198 B1 | 1/2001 | Schulze et al. |
| 8,456,182 B2 | 6/2013 | Bar-Tal et al. |

(Continued)

FOREIGN PATENT DOCUMENTS

| | | |
|---|---|---|
| EP | 2352421 A1 | 5/2010 |
| WO | WO 2008/032291 A2 | 3/2008 |

OTHER PUBLICATIONS

Bifulco, Paolo et al., "Telemedicine supported by Augmented Reality: an interactive guide for untrained people in performing an ECG test", BioMedical Engineering OnLine, Nov. 21, 2014, p. 153, vol. 13, No. 1.

(Continued)

*Primary Examiner* — Stephen P Coleman (57) ABSTRACT

A method for electrode placement includes acquiring an image of a body of a patient, such that the image captures a patch that has been placed on the body. Based on the acquired image and the patch appearing therein, one or more preferred locations are calculated on the body for placing one or more respective electrodes to be used in carrying out a procedure in an internal organ of the patient. The preferred locations are displayed to an operator.

15 Claims, 4 Drawing Sheets

(56) References Cited

U.S. PATENT DOCUMENTS

| | | |
|---|---|---|
| 8,460,189 B2 | 6/2013 | Libbus et al. |
| 8,478,388 B2 | 7/2013 | Nguyen et al. |
| 2010/0049037 A1 | 2/2010 | Pinter et al. |
| 2011/0152987 A1 | 6/2011 | Wahlgren et al. |
| 2011/0208044 A1 | 8/2011 | Edwards et al. |
| 2012/0203091 A1* | 8/2012 | Kinrot .................. A61B 5/0265 600/383 |
| 2013/0204134 A1* | 8/2013 | Harks .................. A61B 5/0084 600/439 |
| 2014/0139405 A1 | 5/2014 | Ribble et al. |
| 2014/0194760 A1 | 7/2014 | Albert |
| 2014/0276167 A1 | 9/2014 | Dasgupta |
| 2015/0141798 A1 | 5/2015 | Bar-Tal |
| 2016/0136415 A1 | 5/2016 | Bunch |

OTHER PUBLICATIONS

Anonymous: "TENS (transcutaneous electrical nerve stimulation)", Retrieved from the Internet: http://www.nhs.uk/Conditions/tens/pages/Introduction.aspx, Aug. 17, 2017.

* cited by examiner

METHOD AND SYSTEM FOR DETERMINING LOCATIONS OF ELECTRODES ON A PATIENT BODY

This patent application is a continuation of U.S. patent application Ser. No. 15/130,110 filed on Apr. 15, 2016.

FIELD OF THE INVENTION

The present invention relates generally to body-surface electrodes, and particularly to methods and systems for determining locations on a patient body for placing body-surface electrodes.

BACKGROUND OF THE INVENTION

Body-surface electrodes (BSEs) are used in some medical procedures such as Electrophysiology (EP). Examples of prior art techniques for using and determining locations of the BSEs are provided below.

PCT International publication WO 2008/032291, whose disclosure is incorporated herein by reference, describes an adhesive electrode patch assembly, in particular for use in impedance measurements with at least one electrode patch that comprises at least one feeding electrode and at least one sensing electrode arranged in pairs, respectively wherein one feeding electrode and one sensing electrode are combined in a single electrode plate.

U.S. Patent Application Publication 2011/0152987, whose disclosure is incorporated herein by reference, describes a placement device for a medical patch that includes an alignment guide having a shaft with a first end having a first anatomical alignment marker and a second end having a second anatomical alignment marker, a swinging gate both pivotally and rotationally coupled with the first end of the shaft for selectively pivoting the gate toward and away from the shaft and rotating the gate between opposite sides of the shaft, whereby the gate has first and second major faces and a first opening extending through the gate between the first and second major faces.

European Patent Application Publication EP2352421, whose disclosure is incorporated herein by reference, describes systems and methods for sensing electrical activity of a patient. In one embodiment, a sensor array system includes a plurality of elongated strips of a flexible substrate material that extend from a first end to terminate in a second end spaced therefrom by a length of the substrate material having spaced apart side edges. A plurality of electrically conductive sensors are connected with and distributed along the length of each of the plurality of elongated strips to provide a column of sensors along each respective strip.

U.S. Pat. No. 8,478,388, whose disclosure is incorporated herein by reference, describes a method for accessing cardiac information acquired via a catheter located at various positions in a venous network of a heart of a patient wherein the cardiac information comprises position information with respect to time for one or more electrodes of the catheter. The method includes performing a principal component analysis on at least some of the position information, and selecting at least one component of the principal component analysis to represent an axis of a cardiac coordinate system.

U.S. Patent Application Publication 2014/0139405, whose disclosure is incorporated herein by reference, describes an augmented reality system that comprises a user interface system, a care facility network, and a medical device. The network is in communication with the user interface system. The medical device is configured to be used with a patient and is in communication with the user interface system. The user interface system receives information from the care facility network and the medical device and displays the information in a user's field of vision.

SUMMARY OF THE INVENTION

An embodiment of the present invention that is described herein provides a method for electrode placement including acquiring an image of a body of a patient, such that the image captures a patch that has been placed on the body. Based on the acquired image and the patch appearing therein, one or more preferred locations are calculated on the body for placing one or more respective electrodes to be used in carrying out a procedure in an internal organ of the patient. The preferred locations are displayed to an operator.

In some embodiments, calculating the preferred locations includes estimating a dimension of the body based on the image, and calculating the preferred locations depending on the dimension of the body. In other embodiments, calculating and outputting the preferred locations includes calculating and outputting, based at least on the estimated dimension of the body, a virtual frame within which the one or more respective electrodes are to be placed. In yet other embodiments, the patch has a predefined physical size, and estimating the dimension of the body includes assessing the dimension of the body based on the predefined physical size of the patch and on an imaged size of the patch in the image.

In an embodiment, the patch includes an embedded electrode, to be used together with the one or more respective electrodes in carrying out the procedure. In another embodiment, carrying out the procedure includes measuring impedance of the body between a distal-end of a catheter located in the internal organ and at least one of the electrodes. In yet another embodiment, calculating and outputting the preferred locations includes calculating and outputting a respective forbidden zone around at least one of the respective electrodes, in which other patches are not to be placed.

In some embodiments, calculating and outputting the respective forbidden zone calculating and outputting a first forbidden zone having a first size for a first type of electrode, and a second forbidden zone having a second size, different from the first size, for a second type of electrode that is different from the first type. In other embodiments, calculating and outputting the preferred locations receiving at least first and second images in which the body appears at different respective positions, and overlaying the preferred locations over the body in the at least first and second images while compensating for the different positions. In yet other embodiments, the method includes, after the electrodes have been placed on the body, acquiring another image of the body and automatically verifying, using the additional image, that the electrodes have been placed in compliance with the calculated preferred locations.

There is additionally provided, in accordance with an embodiment of the present invention, a medical apparatus including a camera and a processor. The camera is configured to acquire an image of a body of a patient, such that the image captures a patch that has been placed on the body. The processor is configured to calculate, based on the acquired image and the patch appearing therein, one or more preferred locations on the body for placing one or more respective electrodes to be used in carrying out a procedure in an internal organ of the patient, and output the preferred locations to an operator.

The present invention will be more fully understood from the following detailed description of the embodiments thereof, taken together with the drawings in which:

DETAILED DESCRIPTION OF EMBODIMENTS

Overview

Medical procedures, such as electrophysiology (EP), may involve placing one or more body-surface electrodes (BSEs) on the patient body. Example BSEs include electrocardiogram (ECG) electrodes and advanced current localization (ACL) electrodes used for locating an intra-body device such as a catheter. Each BSE is typically coupled to a patch that a medical operator may place on the patient's torso.

In an ACL-based EP procedure, for example, a physician inserts a catheter to a patient's heart and uses multiple ACL electrodes for measuring the body impedance between each of the ACL electrodes and a distal end of the catheter. Integration of the impedance measurements allows tracking the location of the distal end.

Correct placement of the patches on the patient's torso, e.g. with respect to the patient's heart, is important for the accuracy and reliability of the procedure. Sometimes, at least one of the patches is not placed accurately, in which case the medical operator has to elevate the patient from an operating table and to rearrange the misplaced patches on the patient's torso. The patch rearrangement causes discomfort to the patient, unnecessarily extends the medical procedure and consumes expensive resources such as occupancy of one or more medical operators and an operating room (OR) in which the procedure is carried out.

Embodiments of the present invention that are described hereinbelow provide improved techniques for accurately determining locations for placing the BSEs on the patient's torso. In the disclosed techniques, an image that includes a calibration patch serves as a reference image for determining the locations of the BSEs on the patient body.

In some embodiments, the medical operator places a calibration patch, of predefined physical dimensions, on the patient's torso. The operator acquires a reference image that captures the torso and the calibration patch, e.g., using a smartphone that comprises a camera and a software application executed by the smartphone's processor. The processor estimates the dimensions of the torso, using the reference image and the known patch dimensions, and determines one or more preferred locations for placing the BSEs on the patient's torso.

In some embodiments it is desirable to maintain a certain clearance zone around each BSE, e.g., in order to reduce interference. In an embodiment, the processor outputs an image including the preferred locations to the smartphone's screen and adds to the image, using augmented reality, a respective virtual clearance zone around at least one of the BSE. In an example embodiment, the processor is configured to calculate the width of the clearance zone based on the type of the respective BSE. In an embodiment, the processor delimits the locations of the three electrodes within a virtual frame, and displays the virtual frame in the image of the patient's torso.

The disclosed techniques determine the desired locations of BSEs a-priori, and eliminate the unnecessary trial-and-error process described above. The disclosed techniques may be carried out before the patient enters the OR, thus saving occupancy and increasing efficiency of the medical operators and OR by shortening the duration of such medical procedures.

System Description

Figure 1:
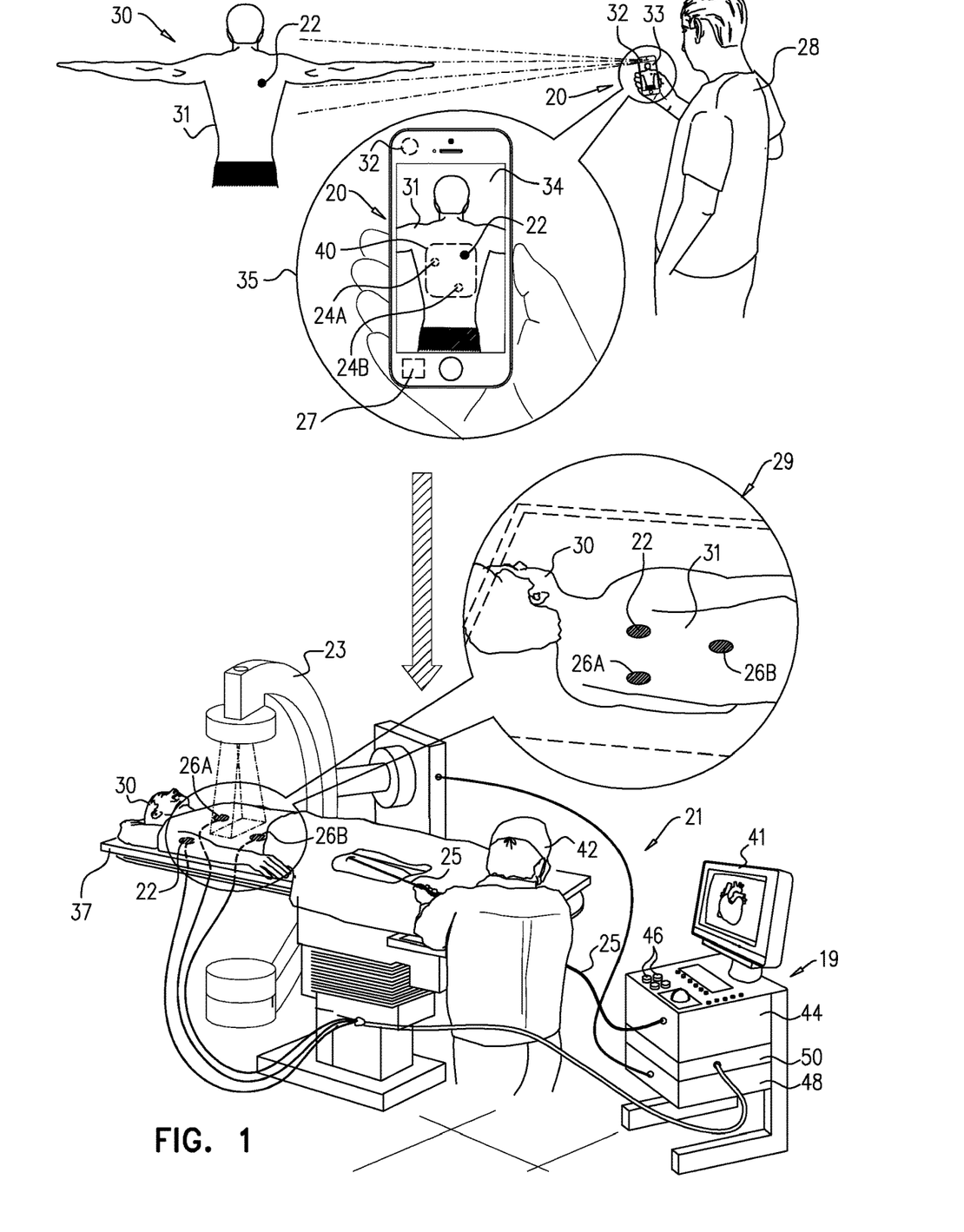
FIG. 1 is a schematic pictorial illustration of a system for determining patch placement on a patient body, in accordance with embodiments of the present invention.

FIG. 1 is a schematic pictorial illustration of a system 20 for determining patch placement in preferred locations on a torso 31 of a patient 30, in accordance with embodiments of the present invention. FIG. 1 further illustrates a fluoroscopic imaging system 23 used for acquiring images of internal organs of patient 30, and a position tracking system 21 applied in a medical procedure, such as ablation or mapping of a heart (not shown) of patient 30.

System 21 comprises a catheter 25, which comprises an electrode on its distal end, and three patches 22, 26A and 26B located on torso 31 as shown in an inset 29. In the example of FIG. 1, position tracking system 21 comprises three advanced current localization (ACL) electrodes (not shown) coupled to three respective patches 22, 26A and 26B. System 21 generates a current from the electrode at the distal end of catheter 25 and uses three impedance measurements taken by the electrodes on patches 22, 26A and 26B to determine the location of the distal end in the patient's heart.

System 21 further comprises a console 19, which comprises a processor 44, an ACL interface 50, an interface 48 for connecting to fluoroscopic imaging system 23, input devices 46, and a display 41. Processor 44 is configured to analyze the measured impedances so as to provide a cardiologist 42 with a position and orientation of the distal end in the heart of patient 30. This method of position tracking is implemented, for example, in the CARTO™ system, produced by Biosense Webster Inc. (Diamond Bar, Calif.) and is described in detail in U.S. Pat. No. 8,456,182, and in U.S. Patent Application Publication 2015/0141798 A1, whose disclosures are all incorporated herein by reference.

When using system 21, one of the challenges is to place patches 22, 26A and 26B accurately on torso 31 so as to allow accurate tracking of the distal end of catheter 25. As depicted in inset 29, during the medical procedure patient 30 is typically anesthetized and positioned with his torso facing an operating table 37. If one or more of the patches are not positioned accurately, cardiologist 42 has to elevate patient 30 from the table and rearrange the patches to their optimal positions. Patch rearrangement encumbers and prolongs the procedure and reduces the efficiency of the operating room (OR).

Embodiments of the present invention that are described herein provide methods and apparatus for accurately placing patches 22, 26A and 26B on torso 31 during preparations for the medical procedure. The disclosed techniques save time of the OR and medical staff and improve the tracking accuracy of the distal end in system 21.

A medical operator, such as a nurse 28, places patch 22 that has predefined dimensions (e.g., diameter in case the patch is round) on torso 31. Patch 22 is referred to herein as a calibration patch.

Referring to an inset 35, system 20 (e.g., a smartphone) comprises a camera 32, which is configured to acquire an image 34 of patient 30, and a display 33. In some embodiments, image 34 captures torso 31 and patch 22 located thereon. System 20 further comprises a processor 27, which is configured to receive image 34 and to estimate the dimensions of torso 31 based on the known dimensions of patch 22.

In an embodiment, processor 27 is further configured to calculate preferred locations 24A and 24B for placing patches 26A and 26B, respectively, on torso 31. Processor 27 then presents, on display 33, patch 22 and locations 24A and 24B overlaid on image 34 using augmented reality. Processor 27 may apply a set of predefined rules, criteria and/or priorities for placing the patches. These may originate, for example, from manufacturer guidelines.

During the image acquisition, torso 31 may move relative to system 20. For example, patient 30 or the hand of nurse 28 may move, thus, displayed locations 24A and 24B may need to shift to compensate for such movements. In an augmented reality implementation, processor 27 receives and processes a streaming video from camera 32, and continuously recalculates and displays updated overlaid positions of preferred locations 24A and 24B on torso 31. In other words, the user (e.g., nurse 28) will thus see, on display 33, graphical representations of preferred locations 24A and 24B, which are overlaid on the same locations on torso 31, regardless of movement of the torso in the image.

In an embodiment, processor 27 may additionally display a virtual frame 40 on image 34. Frame 40 determines a permitted area for placing patches 22, 26A and 26B. In other words, processor 27 advises the user not to place patches outside frame 40. As described above, processor 27 may apply augmented reality techniques so that the position of virtual frame 40 will be displayed in a fixed position relative to torso 31, regardless of motion of torso 31 relative to system 20. The above techniques of system 20 are described in detail in FIGS. 2-4 below.

Embodiments of the present invention may be used with ACL electrodes, as well as with other types of body-surface electrodes such as defibrillation and electrocardiogram (ECG) electrodes. For simplicity and clarity, except where otherwise stated, the following description refers to ACL electrodes. The process can be adapted, mutatis mutandis, for other types of electrodes.

The configuration of system 20 shown in FIG. 1 is an example configuration that is depicted purely for the sake of conceptual clarity. In alternative embodiments, any other suitable system configuration can be used. For example, the disclosed techniques are not limited to implementation using a smart-phone. In an alternative embodiment, image 34 may be acquired by a standalone camera, and imported into system 21. The functions of processor 27 may then be carried out by processor 44 of system 21, and the results presented on display 41.

Processor 27 and/or processor 44 typically comprise general-purpose processors, which are programmed in software to carry out the functions described herein. The software may be downloaded to the processor or processors in electronic form, over a network, for example, or it may, alternatively or additionally, be provided and/or stored on non-transitory tangible media, such as magnetic, optical, or electronic memory.

Figure 2:
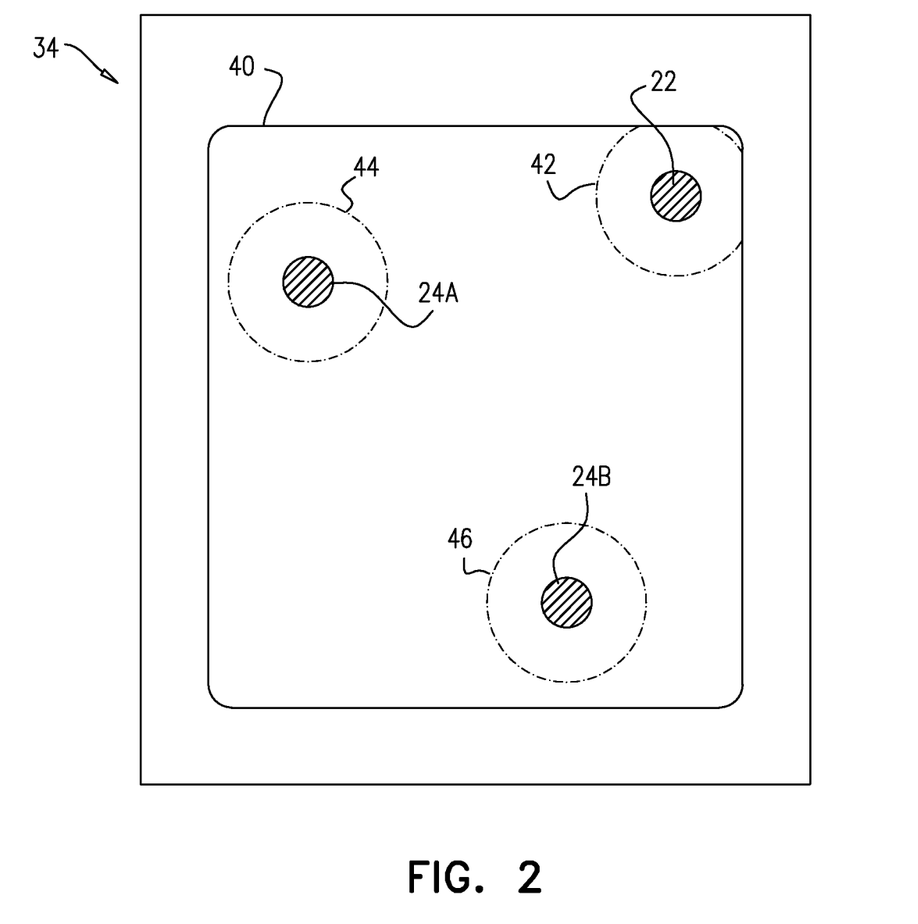
FIG. 2 is a schematic pictorial illustration of an image captured for determining patch placement on a patient body, in accordance with embodiments of the present invention.

FIG. 2 is a schematic pictorial illustration of image 34 as displayed on display 33 of system 20, in accordance with embodiments of the present invention. Image 34 shows patch 22 as placed by nurse 28 on torso 31 of patient 30. In some embodiments, patch 22 is used as a reference for estimating the dimensions of torso 31 as described above. In some embodiments, patch 22 may comprise an electrode, such as an ACL electrode, which is used in the localization process together with electrodes 26A and 26B.

Image 34 further shows locations 24A and 24B calculated by processor 27 and virtually displayed, using augmented reality, so as to provide nurse 28 with optimal locations for placing patches 26A and 26B. Processor 27 receives real-time video streaming of torso 31 and patch 22 from camera 32. In case torso 31 moves relative to camera 31, the previously calculated position of locations 24A and 24B is not accurate. In an embodiment, processor 27 uses the augmented reality techniques to correctly present the overlaid positions of locations 24A and 24B on torso 31, in real-time even when relative movements occur. Thus, the system provides nurse 28 with the correct preferred locations for placing patches 26A and 26B on torso 31. Patches 22, 26A and 26B typically comprise electrodes of the same type (e.g., ACL) but may comprise any suitable combination of same or different electrode types. In other embodiments, patch 22 does not comprise an electrode, and is used only for calibration.

In some embodiments, processor 27 is configured to define virtual clearance zones 42, 44 and 46 around patches 22, 26A and 26B, respectively. Typically, the type of electrode determines the width of the respective clearance zone. The clearance zone defines a restricted area around the respective patch that in which other patches should not be positioned, so as to allow optimized operation of the respective electrode. For example, in case of ACL electrodes, the clearance zone allows the detection of signals used for measuring the impedance between the distal end and the respective ACL electrode, without being exposed to unrelated surrounding interfering signals.

In other embodiments, processor 27 calculates frame 40 that defines an area in which patches 22, 26A and 26B are delimited on torso 31. As described above, system 21 generates a current from the electrode located in the distal end of catheter 25 and measures the distribution of the impedances as measured by patches 22, 26A and 26B. The measured impedances are typically used for determining the location of the distal end in the patient's heart. Thus, it is important that patches 22, 26A and 26B are located within a predefined mutual proximity so as to provide processor 44 with impedance signals that allow accurate calculation and tracking of the distal end in the patient's heart.

Figure 3:
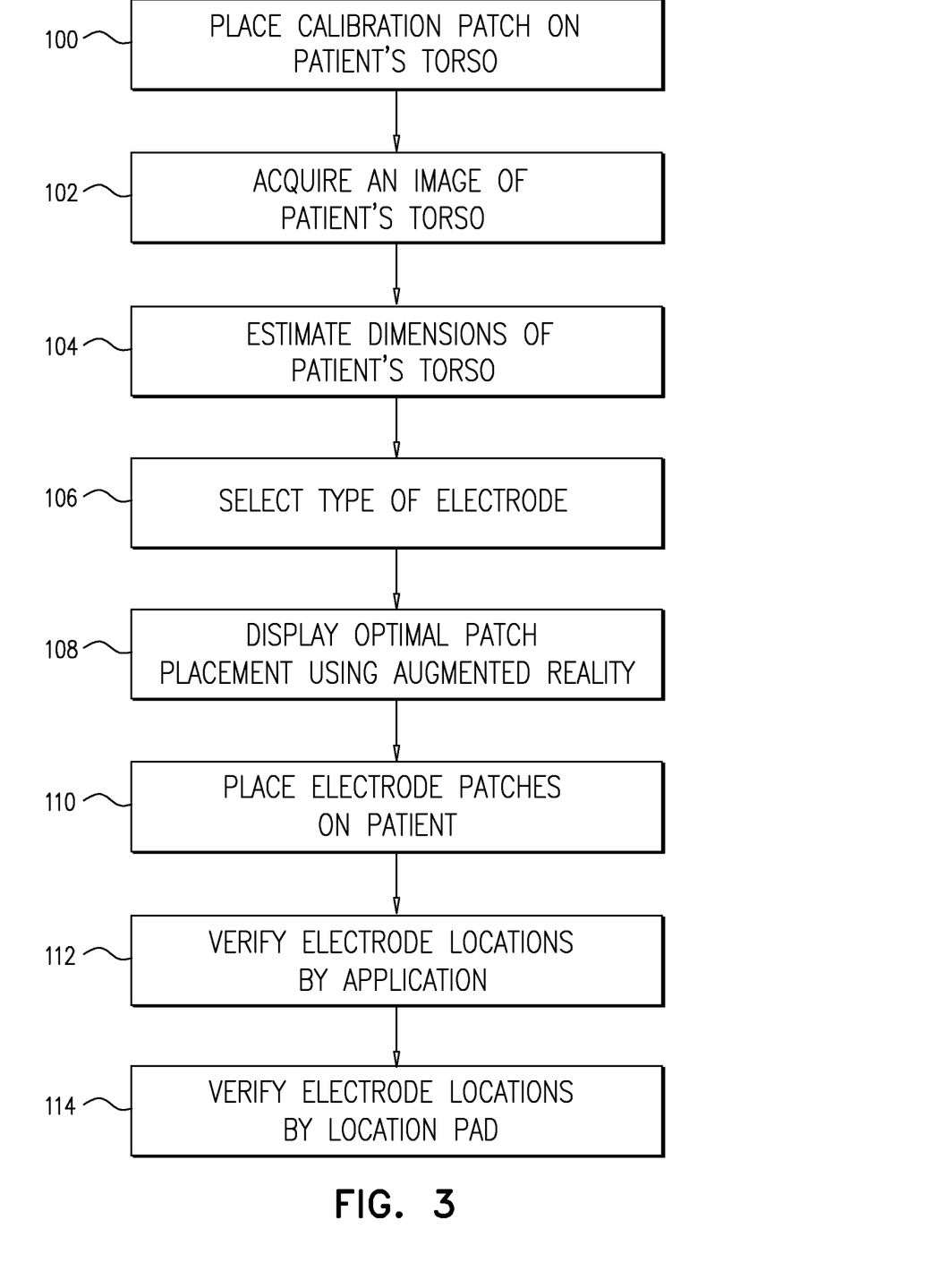
FIGS. 3 and 4 are flow charts that schematically illustrate methods for determining locations for placing electrodes on a patient body, in accordance with embodiments of the present invention.

FIG. 3 is a flow chart that schematically illustrates a method for placing electrodes on torso 31 of patient 30, in accordance with embodiments of the present invention. The method begins at a calibration patch placement step 100, in which nurse 28 places patch 22 on torso 31 of patient 30. In some embodiments, steps 100 to 112 are carried out before patient 30 enters the operating room (OR) while patient 30 is typically in full consciousness and cooperating with nurse 28.

At an image acquisition step 102, patient may stand and optionally lift his/her arms while nurse 28 directs camera 32 to capture image 34 of torso 31 as shown in FIG. 1. Image 34, as it appears on display 33, captures the entire torso 31 and patch 22 located thereon (also shown in inset 35 of FIG. 1).

Patch 22 typically comprises a preselected type of electrode (e.g., ACL) or may be only a patch used for calibration. At a torso estimation step 104, processor 27 analyses image 34 and estimates, based on the size of patch 22, the dimensions of torso 31. At an electrode selection step 106, a type of electrode patches (e.g., patches 26A and 26B) is selected. In some embodiments, the type may be predefined as an input from an external source (e.g., a host computer). In alternative embodiments, nurse 28 may select the electrode type from a menu or match the selected type to patch 22.

The type of electrode in patches 22, 26A and 26B determines respective clearance zones 42, 44 and 46. The clearance zone defines the minimal area around a respective patch that should remain empty of other patches so as to obtain clear impedance signals between the distal end of catheter 25 and the respective patch, and to minimize interfering signals from external sources. Furthermore, patches 22, 26A and 26B must be located within a predefined mutual proximity (e.g., within virtual frame 40) so that processor 44 of system 21 is able to calculate the location of the distal end based on the inputs from the three respective ACL electrodes.

At a display step 108, processor 27 calculates the position of the patient's heart based on the calculated dimension of torso 31. The ACL electrodes should typically be placed around the patient's heart. Thus, processor 27 calculates optimal locations 24A and 24B for placing respective patches 26A and 26B and displays the locations on display 33. In some embodiments, processor 27 may use augmented reality to virtually add locations 24A and 24B to image 34. In other embodiments, processor 27 may add to image 34 virtual clearance zones 42, 44 and 46 around patch 22, and locations 24A and 24B, respectively. In yet other embodiments, processor 27 may add to image 34 virtual frame 40 that defines the delimited area for placing patches 26A and 26B.

The dimensions of clearance zones 42, 44 and 46 and virtual frame 40 depend on the medical procedure and on the selected type of electrode in patches 22, 26A and 26B, so as to allow optimal operational conditions of system 21 during the medical procedure.

At an electrode placement step 110, in an embodiment, nurse 28 places patches 26A and 26B on torso 31 in accordance with the augmented reality display as described at display step 108.

At a position verification step 112, nurse 28 directs camera 32 to torso 31, optionally acquires a second image, and respectively compares virtual locations 24A and 24B as proposed by system 20 and the actual positions at which patches 26A and 26B were placed while patch 22 serves as an anchor. In addition, nurse 28 verifies that patches 22, 26A and 26B are located within frame 40. In some embodiments, processor 27 may calculate the placement deviation and alert nurse 28 in case at least one of patches 26A and 26B is not placed accurately with respect to virtual locations 24A and 24B and frame 40. Processor 27 may recommend nurse 28 to reposition at least one of the patches so as to optimize the placement of patches 22, 26A and 26B.

In other embodiments, nurse 28 may recognize a placement violation in image 34, and in response may reposition at least one of the respective patches to match the designated location.

After position verification step 112, patient 30 is transferred into the OR and placed on table 37. At a final verification step 114, cardiologist 42 uses system 21 to verify that patches 22, 26A and 26B are placed accurately. In an embodiment, system 21 comprises a magnetic positioning system (not shown) that comprises a location pad (not shown) on table 37 facing torso 31. Cardiologist 42 may insert catheter 25 and compare the location of the distal end as obtained by the ACL and the magnetic position tracking systems to verify that patches 22, 26A and 26B are placed accurately on torso 31.

Figure 4:
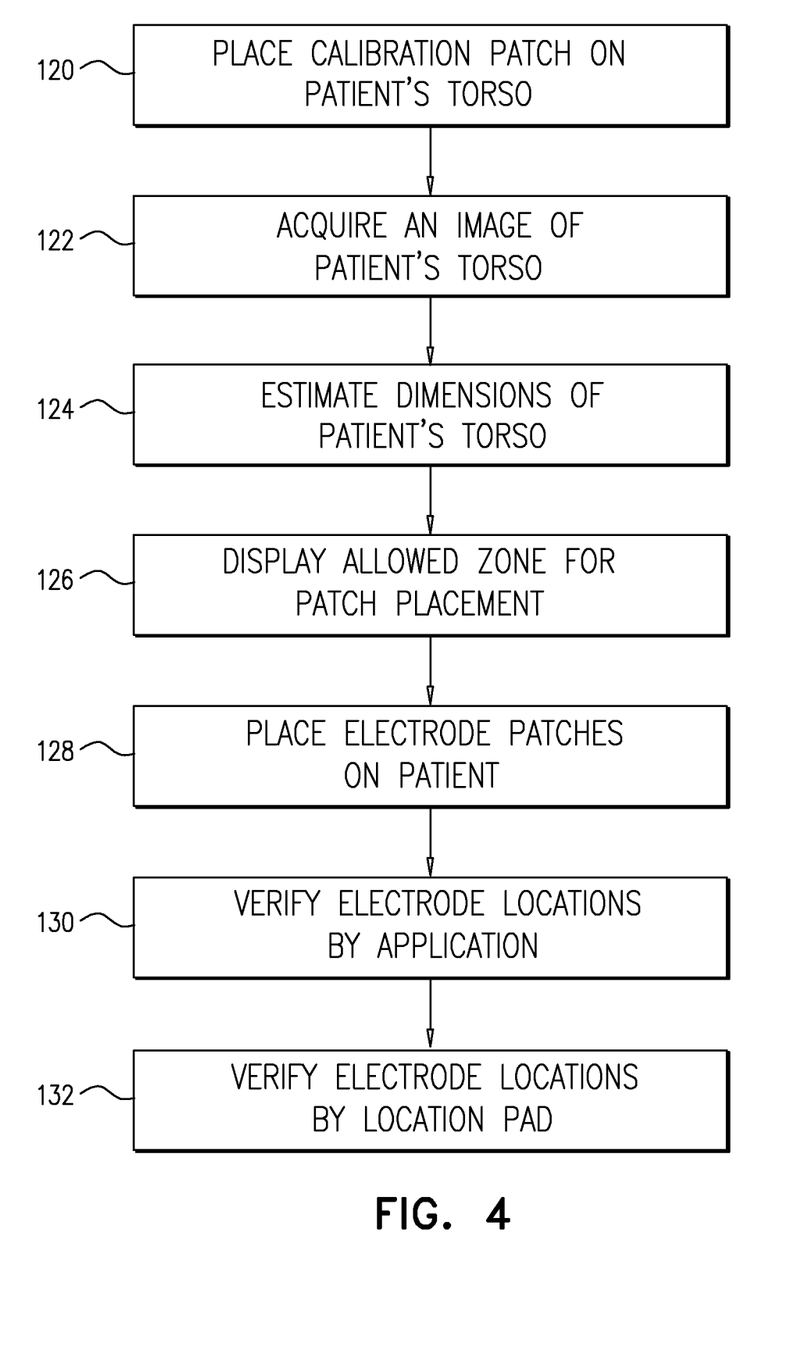

FIG. 4 is a flow chart that schematically illustrates a method for placing electrodes on torso 31 of patient 30, in accordance with other embodiments of the present invention. The method begins at a calibration patch placement step 120, in which nurse 28 places patch 22 on torso 31 of patient 30 as described in patch placement step 100 at FIG. 3. At an image acquisition step 122, patient 30 may stand and optionally lift his/her arms while nurse 28 directs camera 32 to capture image 34 of torso 31 as shown in FIG. 1 and as described in image acquisition step 102 above.

At a torso estimation step 124, as described above at a torso estimation step 104, processor 27 analyses image 34 and estimates, based on the known dimensions of patch 22, the dimensions of torso 31. At an allowed zone display step 126, processor 27 calculates an allowed zone for placing patches 26A and 26B and marks the allowed zone as virtual frame 40 in image 34 so that nurse 28 may place patches 26A and 26B within frame 40.

At an electrode placement step 128, nurse 28 places patches 26A and 26B on patient 30 torso within frame 40 as described at allowed zone display step 126. In an embodiment, processor 27 may display clearance zones 42, 44 and 46 so that nurse 28 does not place patches 26A and 26B too close to one another or to patch 22.

At a position verification step 130, nurse 28 captures a second image of torso 31 with patches 22, 26A and 26B located thereon. In an embodiment, nurse 28 checks whether patches 22, 26A and 26B are located within frame 40. In another embodiment, processor 27 may alert nurse 28 to reposition at least one of the patches so as to obtain optimal placement of patches 22, 26A and 26B. At a final verification step 132, cardiologist 42 uses system 21 to verify that patches 22, 26A and 26B are placed accurately as described in verification step 114 above.

The processes above are given purely by way of example. In alternative embodiments, the disclosed techniques can be carried out in any other suitable manner. Although the examples above refer to placement of three electrodes on the patient torso, the disclosed techniques can be used for placing a smaller or larger number of electrodes, as desired, on any part of the patient body.

Although the embodiments described herein mainly address cardiology applications, the methods and systems described herein can also be used in other applications, such as in skin sensitivity testing.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for body surface electrode placement, comprising:

acquiring an image of a torso of a body of a patient, such that the image captures a calibration patch having known dimensions that has been placed on the torso of the body;

estimating the dimensions of the patient's torso based upon the known dimensions of the calibration patch;

calculating, a priori, based on the acquired image and the calibration patch appearing therein along with the dimensions of the patient's torso, one or more preferred locations on the torso of the body for placing one or more respective body surface electrodes to be used in carrying out a procedure in an internal organ of the patient including calculating clearance zones around each of the one or more respective body surface electrodes based upon the type of the one or more respective body surface electrodes to eliminate interference between the one or more body surface electrodes; and outputting the preferred locations to an operator.

2. The method according to claim 1, wherein calculating the preferred locations comprises estimating a dimension of the body based on the image, and calculating the preferred locations depending on the dimension of the body.

3. The method according to claim 2, wherein calculating and outputting the preferred locations comprises calculating and outputting, based at least on the estimated dimension of the body, a virtual frame within which the one or more respective body surface electrodes are to be placed.

4. The method according to claim 2, wherein the patch has a predefined physical size, and wherein estimating the dimension of the body comprises assessing the dimension of the body based on the predefined physical size of the patch and on an imaged size of the patch in the image.

5. The method according to claim 1, wherein the patch comprises an embedded electrode, to be used together with the one or more respective body surface electrodes in carrying out the procedure.

6. The method according to claim 1, wherein carrying out the procedure comprises measuring impedance of the body between a distal-end of a catheter located in the internal organ and at least one of the body surface electrodes.

7. The method according to claim 1, wherein calculating and outputting the preferred locations comprises receiving at least first and second images in which the body appears at different respective positions, and overlaying the preferred locations over the body in the at least first and second images while compensating for the different positions.

8. The method according to claim 1, and comprising, after the body surface electrodes have been placed on the body, acquiring another image of the body and automatically verifying, using the additional image, that the body surface electrodes have been placed in compliance with the calculated preferred locations.

9. A medical apparatus, comprising:

a camera, which is configured to acquire an image of a torso of a body of a patient, such that the image captures a calibration patch having known dimensions that has been placed on the torso of the body; and a processor, which is configured to:

estimate the dimensions of the patient's torso based upon the known dimensions of the calibration patch;

determine, a priori, based on the acquired image and the calibration patch appearing therein along with the dimensions of the patient's torso, one or more preferred locations on the torso of the body for placing one or more respective body surface electrodes to be used in carrying out a procedure in an internal organ of the patient by calculating clearance zones around each of the one or more respective electrodes based upon the type of the one or more respective body surface electrodes to eliminate interference between the one or more body surface electrodes; and output the preferred locations to an operator.

10. The medical apparatus according to claim 9, wherein the processor is configured to estimate a dimension of the body based on the image, and to calculate the preferred locations depending on the dimension of the body.

11. The medical apparatus according to claim 10, wherein the processor is configured to calculate and output, based at least on the estimated dimension of the body, a virtual frame within which the one or more respective body surface electrodes are to be placed.

12. The medical apparatus according to claim 10, wherein the patch has a predefined physical size, and wherein the processor is configured to assess the dimension of the body based on the predefined physical size of the patch and on an imaged size of the patch in the image.

13. The medical apparatus according to claim 9, wherein the patch comprises an embedded electrode, to be used together with the one or more respective body surface electrodes in carrying out the procedure.

14. The medical apparatus according to claim 9, wherein carrying out the procedure comprises measuring impedance of the body between a distal-end of a catheter located in the internal organ and at least one of the body surface electrodes.

15. The medical apparatus according to claim 9, wherein the processor is configured to receive at least first and second images in which the body appears at different respective positions, and to overlay the preferred locations over the body in the at least first and second images while compensating for the different positions.

* * * * *